United States Patent [19]
Lotti et al.

[11] Patent Number: 5,219,849
[45] Date of Patent: Jun. 15, 1993

[54] SUBSTITUTED PYRAZINES, PYRIMIDINES AND PYRIDAZINES FOR USE IN THE TREATMENT OF GLAUCOMA

[75] Inventors: Victor Lotti, Harleysville, Pa.; Graham A. Showell, Welwyn Garden City, Great Britain

[73] Assignee: Merck Sharp & Dohme, Hertfordshire, United Kingdom

[21] Appl. No.: 809,612

[22] Filed: Dec. 17, 1991

[30] Foreign Application Priority Data

Dec. 21, 1990 [GB] United Kingdom ............... 9027863
Dec. 21, 1990 [GB] United Kingdom ............... 9027878
Jun. 7, 1991 [GB] United Kingdom ............... 9112274
Jun. 7, 1991 [GB] United Kingdom ............... 9112309

[51] Int. Cl.$^5$ ............... A61K 31/55; A61K 31/495; C07D 223/00; C07D 295/00; C07D 237/00; C07D 401/00
[52] U.S. Cl. ................... 514/214; 514/254; 514/256; 514/269; 514/913; 540/582; 544/238; 544/239; 544/333; 544/298; 544/405

[58] Field of Search ............... 544/238, 333, 405, 239, 544/298; 514/254, 256, 214, 269, 913; 540/582

[56] References Cited

FOREIGN PATENT DOCUMENTS 327155 1/1989 European Pat. Off. .
370415 11/1989 European Pat. Off. .
384288 2/1990 European Pat. Off. .

OTHER PUBLICATIONS

Drugs, 1979, vol. 17, 38.
Drugs, and Ther., Bull., 1989, vol. 21, 85.

Primary Examiner—Cecilia Tsang
Attorney, Agent, or Firm—Robert J. North; Joseph F. DiPrima

[57] ABSTRACT

A class of pyrazine, pyrimidine and pyridazine derivatives, substituted by a non-aromatic azabicyclic ring system and optionally by up to two further substituents, is of use in the preparation of medicaments, especially formulations adapted for topical administration to the eye, suitable for the treatment of glaucoma and/or for reducing intraocular pressure.

8 Claims, No Drawings

SUBSTITUTED PYRAZINES, PYRIMIDINES AND PYRIDAZINES FOR USE IN THE TREATMENT OF GLAUCOMA

The present invention relates to a class of substituted pyrazine, pyridazine and pyrimidine compounds for use in the treatment of glaucoma and to certain novel compounds having such use, formulations containing them and their synthesis.

Glaucoma is an ocular disorder associated with elevated intraocular pressures which are too high for normal function and may result in irreversible loss of visual function. If untreated, glaucoma may eventually lead to blindness. Ocular hypertension, i.e. the condition of elevated intraocular pressure without optic field defects, is now believed by many ophthalmologists to represent the earliest phase of glaucoma.

Many of the drugs formerly used to treat glaucoma proved not entirely satisfactory. Topical administration to the eye of agents such as pilocarpine may be used in order to improve the outflow of aqueous humour and reduce the intraocular pressure (see Drugs, 1979, vol. 17, 38; and Drugs and Ther. Bull., 1989, vol. 21, 85), but these have associated side effects such as emesis and myosis.

We have now found compounds which lower the intraocular pressure without exhibiting side effects to the extent associated with hitherto-known drugs used against glaucoma which act through cholinergic mechanisms.

EP-A-0327155 describes a class of compounds useful in the treatment of certain neurological and mental illnesses such as Alzheimer's disease. This class includes compounds which are pyrazines, pyridazines or pyrimidines, or salts or prodrugs thereof, substituted on one of the ring carbon atoms thereof with a non-aromatic azacyclic or azabicyclic ring system; and independently substituted on each of the other ring carbon atoms with a substituent of low lipophilicity of a hydrocarbon substituent. We have tested some of these compounds and found that they effect reduction of intraocular pressure without exhibiting severe adverse effects on pupil size.

The compounds for use according to the present invention may be represented by structural formula (I):

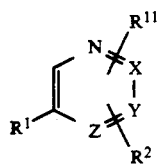

(I)

or a salt or prodrug thereof; wherein one of X, Y and Z represents nitrogen and the remainder represent carbon atoms;

$R^1$ represents a non-aromatic azabicyclic ring system selected from:

 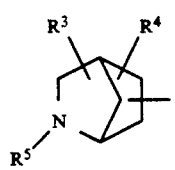 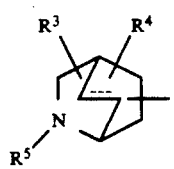

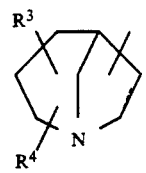 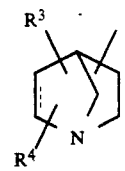

wherein the broken line represents an optional chemical bond;

the substituents $R^3$ and $R^4$ may be present at any position, including the point of attachment to the pyrazine, pyridazine or pyrimidine ring, and independently represent hydrogen, $C_{1-4}$ alkyl, halogen, $C_{1-4}$ alkoxy, hydroxy, carboxy or $C_{1-4}$ alkoxycarbonyl; or $R^3$ and $R^4$ together represent carbonyl; and $R^5$ represents hydrogen or $C_{1-4}$ alkyl; and $R^2$ and $R^{11}$ independently represent hydrogen, halogen, $-CF_3$, $-OR^6$, $-NR^6R^7$, $-CN$, $C_{1-8}$ alkyl or $C_{2-8}$ alkenyl; wherein $R^6$ is hydrogen or $C_{1-6}$ alkyl; and $R^7$ is hydrogen or $C_{1-6}$ alkyl.

In the definition of $R^1$, it will be appreciated that the nitrogen atom in the azabicyclic ring system will carry a lone pair of electrons.

In the definition of $R^2$ and/or $R^{11}$, unless otherwise specified, "alkyl" and "alkenyl" groups may be straight, branched or cyclic groups.

The compounds for use according to this invention may be represented by structural formulae (IA), (IB) or (IC):

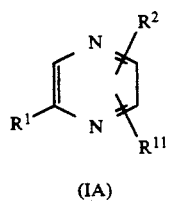 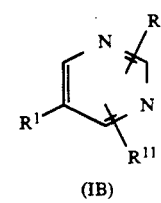 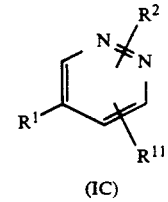

(IA)         (IB)         (IC)

or salts or prodrugs thereof; wherein $R^1$, $R^2$ and $R^{11}$ are as defined above.

Preferably, the ring is a pyrazine of formula (IA), i.e. having the nitrogen atoms at the 1,4 positions.

One subclass of compounds for use according to the present invention is represented by formula (II):

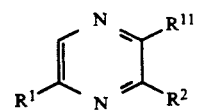

(II)

wherein $R^1$, $R^2$ and $R^{11}$ are as defined above.

Suitably the azabicyclic ring system is azanorbornane, quinuclidine, isoquinuclidine, azabicyclo[2.2.2]octene or 1-azabicyclo[3.2.1]octane, any of which may in particular be either unsubstituted or substituted with methyl, hydroxy, fluoro, chloro or methoxycarbonyl.

Suitably the group $R^3$ is hydrogen or methyl; and $R^4$ is hydrogen, $C_{1-4}$ alkoxy, $C_{1-4}$ alkyl, $C_{1-4}$ alkoxycarbonyl, halogen or hydroxy, preferably methoxy, methyl, fluoro, chloro, hydroxy or methoxycarbonyl. Preferably one or both of $R^3$ and $R^4$ is hydrogen.

Preferably the group $R^5$ represents hydrogen or methyl.

Preferably the groups $R^2$ and $R^{11}$ independently represent hydrogen, halogen, $-CF_3$, $-OR^6$, $-NHR^6$, $-CN$, $C_{1-6}$ alkyl, $C_{1-6}$ cycloalkyl or $C_{2-6}$ alkenyl. Particular values of the groups $R^2$ and/or $R^{11}$ are hydrogen, chloro, bromo, methyl, ethyl, isopropyl, cyclopropyl, methoxy, ethoxy, isopropoxy and n-butoxy.

For example, $R^1$ may be 1-azabicyclo[2.2.1]heptane, quinuclidine or isoquinuclidine;

$R^3$, $R^4$ and $R^5$ may be hydrogen;

$R^2$ and/or $R^{11}$ may be hydrogen, halo, $-CF_3$, $-OR^6$ or $C_{1-8}$ alkyl; especially when $R^{11}$ is hydrogen or $C_{1-8}$ alkyl.

One group of prodrugs of compounds for use according to this invention have a substituent on the pyrazine, pyridazine or pyrimidine ring which is hydrolysable in vivo to an amino group.

Groups which are hydrolysable in vivo to an amino group on the compounds for use according to this invention may be readily ascertained by administering the compound to a human or animal and detecting, by conventional analytical techniques, the presence of the corresponding compound having an amino substituent in the urine of a human or animal. Examples of such groups include, for example, amido and urethane substituents, in particular a group of formula $-NH.Q$, wherein Q represents CHO, COR or $CO_2R$, and R represents an optionally substituted hydrocarbon group.

In this context, the hydrocarbon group R includes groups having up to 20 carbon atoms, suitably up to 10 carbon atoms, conveniently up to 6 carbon atoms. Suitable groups R include $C_{1-9}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, and aryl($C_{1-6}$)alkyl. The alkyl group R may be straight or branched chain and may contain, for example, up to 12 carbon atoms, suitably from 1 to 6 carbon atoms. In particular the group may be substituted methyl, ethyl, n- or iso-propyl, n-, sec-, iso- or tert-butyl, n- or iso-heptyl, or n- or iso-octyl. Suitable cycloalkyl groups include cyclopentyl and cyclohexyl. The aryl group R includes phenyl and naphthyl optionally substituted with up to five, preferably up to three, substituent groups.

Most of the compounds for use according to this invention have at least one asymmetric centre and often more than one; and can therefore exist as both enantiomers and diastereoisomers. In particular, those compounds possessing an unsymmetrical azabicyclic ring system may exist as exo and endo diastereoisomers. It is to be understood that the invention covers the use of all such isomers and mixtures thereof.

Also included within the scope of the present invention is the use of salts of these compounds. It will be appreciated that salts of the compounds for use in medicine will be non-toxic pharmaceutically acceptable salts. Other salts may, however, be useful in the preparation of the compounds for use according to the invention or their non-toxic pharmaceutically acceptable salts. Acid addition salts, for example, may be formed by mixing a solution of the compound with a solution of a pharmaceutically acceptable non-toxic acid such as hydrochloric acid, fumaric acid, oxalic acid, maleic acid, succinic acid, acetic acid, citric acid, tartaric acid, p-toluenesulphonic acid, carbonic acid or phosphoric acid. Preferred are the hydrochloride, hydrogen oxalate, maleate, tartrate and tosylate salts. Where the compound carries a carboxylic acid group the invention also contemplates salts thereof, preferably non-toxic pharmaceutically acceptable salts thereof, such as the sodium, potassium and calcium salts thereof.

Salts of amine groups may also comprise the quaternary ammonium salts in which the amino nitrogen atom carries an alkyl, alkenyl, alkynyl or aralkyl group.

Examples of compounds for use according to this invention include:

exo-3-(6-methylpyrazin-2-yl)-1-azabicyclo[2.2.1]heptane;

3-(6-methylpyrazin-2-yl)-1-azabicyclo[2.2.2]octane;

exo-3-(3,5-dimethylpyrazin-2-yl)-1-azabicyclo[2.2.1]heptane;

endo-3-(5,6-dimethylpyrazin-2-yl)-1-azabicyclo[2.2.1]heptane;

3-(pyrazin-2-yl)-1-azabicyclo[2.2.2]octan-3-ol;

endo-3-(6-ethoxypyrazin-2-yl)-1-azabicyclo[2.2.1]heptane;

anti-6-(5-methoxypyrazin-2-yl)-2-azabicyclo[2.2.2]octane;

anti-6-(6-methylpyrazin-2-yl)-2-azabicyclo[2.2.2]octane;

endo-3-(6-cyclopropylpyrazin-2-yl)-1-azabicyclo[2.2.1]heptane;

3-(6-bromopyrazin-2-yl)-1-azabicyclo[2.2.2]octane;

and salts and prodrugs thereof.

Some of the compounds having the use according to this invention are novel and therefore the present invention further provides:

anti-6-(5-methoxypyrazin-2-yl)-2-azabicyclo[2.2.2]octane;

anti-6-(6-methylpyrazin-2-yl)-2-azabicyclo[2.2.2]octane;

endo-3-(6-cyclopropylpyrazin-2-yl)-1-azabicyclo[2.2.1]heptane;

3-(6-bromopyrazin-2-yl)-1-azabicyclo[2.2.2]octane;

and salts and prodrugs thereof.

The compounds for use according to this invention including the novel compounds of the invention may be prepared as described in EP-A-0327155 or by processes analogous thereto known to persons skilled in the art.

When administered for the treatment of elevated intraocular pressure or glaucoma, the active compound is preferably administered topically to the eye, although systemic treatment is also possible. The dose administered can be from as little as 0.1 to 25 mg or more per day, singly, or preferably on a 2 to 4 dose per day regimen although a single dose per day is satisfactory.

The present invention therefore also provides a pharmaceutical formulation suitable for use in reducing intraocular pressure or for treating glaucoma which formulation comprises a novel compound of formula (I) and a pharmaceutically acceptable carrier.

It will be understood that any formulation may further comprise another active ingredient such as another antiglaucoma agent for example a topical carbonic anhydrase inhibitor.

When given systemically, the drug can be given by any route, although the oral route is preferred. In oral administration, the drug can be employed in any of the usual dosage forms such as tablets or capsules, either in a contemporaneous delivery or sustained release form. Any number of the usual excipients or tabletting aids can likewise be included.

When given by the topical route, the active compound or an ophthalmologically acceptable salt thereof such as the hydrochloride salt is formulated into an ophthalmic preparation. In such formulations, from 0.0005% to 15% by weight can be employed. The objective is to administer a dose of from 0.1 to 1.0 mg per eye per day to the patient, with treatment continuing so long as the condition persists.

Thus, in an ophthalmic solution, insert, ointment or suspension for topical delivery, or a tablet, intramuscular or intravenous composition for systemic delivery, the active medicament or an equivalent amount of a salt thereof is employed, the remainder being carrier, excipients, preservatives and the like as are customarily used in such compositions.

The active drugs of use in this invention are most suitably administered in the form of ophthalmic administration to the eye such as a suspension, ointment, or as a solid insert. A preferred composition is eye drops. Formulations of these compounds may contain from 0.0005 to 15% and especially 0.05% to 2% of medicament. Higher dosages as, for example, about 10% or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated persists.

This invention therefore further provides a pharmaceutical formulation adapted for topical administration to the eye which formulation comprises a compound of formula (I) and a carrier suitable for topical administration.

These hereinbefore described dosage values are believed accurate for human patients and are based on the known and presently understood pharmacology of the compounds, and the action of other similar entities in the human eye. As with all medications, dosage requirements are variable and must be individualized on the basis of the disease and the response of the patient.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting and bodying agents, for example polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine oleate, polyoxyethylene sorbitan monopalmitylate, dioctyl sodium sulfosuccinate, monothioglycerol, thiosorbitol and ethylenediamine tetraacetic acid. Additionally, suitable ophthalmic vehicles can be used as carrier media for the present purpose including conventional phosphate buffer vehicle systems, isotonic boric acid vehicles, isotonic sodium chloride vehicles and isotonic sodium borate vehicles.

The pharmaceutical formulation may also be in the form of a solid insert such as one which after dispensing the drug remains essentially intact, or a bio-erodible insert that is soluble in lachrymal fluids or otherwise disintegrates.

The present invention will now be illustrated by the following Descriptions and Examples.

Description A:
Exo-3-(6-Methylpyrazin-2-yl)-1-azabicyclo[2.2.1]heptane Sesquioxalate Prepared according to Example 27 of European Patent specification No. 327155.

Description B:
3-(6-Methylpyrazine-2-yl)-1-azabicyclo[2.2.2]octane Hydrogen Oxalate Prepared according to Example 4 of European Patent specification No. 327155.

Description C:
Exo-3-(3,5-Dimethylpyrazin-2-yl)-1-azabicyclo[2.2.1]heptane Dihydrochloride Prepared according to Example 52 of European Patent Specification No. 327155.

Description D:
Endo-3-(5,6-Dimethylpyrazin-2-yl)-1-azabicyclo[2.2.1]heptane Hydrogen Oxalate Prepared according to Example 57 of European Patent specification No. 327155.

Description E:
3-(Pyrazin-2-yl)-1-azabicyclo[2.2.2]octan-3-ol

Prepared according to Example 1 of European Patent specification No. 327155.

Description F:
Endo-3-(6-Ethoxypyrazin-2-yl)-1-azabicyclo[2.2.1]heptane Sesquioxalate Prepared according to Example 32 of European Patent specification NO. 327155.

EXAMPLE 1

Endo-3-(6-Cyclopropylpyrazin-2-yl)-1-azabicyclo[2.2.1]heptane Hydrogen Oxalate a) Tetracyclopropylstannane Iodine (2 crystals was added to magnesium (5.34 g, 0.22 mol) in anhydrous tetrahydrofuran (30 mL). Approximately 1 mL of cyclopropylbromide was added and the mixture heated to 60° C. After the reaction had started the rest of the cyclopropylbromide (total=20 mL, 0.25 mol) was added dropwise over 30 minutes keeping the mixture at gentle reflux. After addition the mixture was stirred at 60° C. for 30 minutes then cooled to room temperature. Tin (IV) chloride (5.8 mL, 0.05 mol) was added dropwise over 20 minutes, then the mixture was heated at reflux for 1 hour. After cooling, water (50 mL) was added cautiously and the mixture was extracted with diethyl ether (4×100 mL). The combined organics were dried (sodium sulphate) and evaporated to give an orange oil which was distilled under vacuum to give the product as a pale yellow oil (3.20 g, 23%), bp 140°–142° C. (18 mmHg).

b) Endo-3-(6-Cyclopropylpyrazin-2-yl)-1-azabicyclo-[2.2.1]heptane Hydrogen Oxalate To a stirred solution of end-3-(6-chloropyrazin-2-yl)-1-azabicyclo[2.2.1]heptane (255 mg, 1.2 mmol; EPA 327155) and tetracyclopropylstannane (368 mg, 1.3 mmol) in dry dimethylformamide (10 mL), under a nitrogen atmosphere, was added potassium carbonate (166 mg, 1.2 mmol) followed by tetrakis (triphenylphosphine) palladium (67 mg, 0.06 mmol) and the mixture was heated to reflux for 1.5 hours. The mixture was evaporated to dryness in vacuo and the residue dissolved in dichloromethane (20 mL) and water (20 mL). The organic layer was separated and the aqueous was re-extracted with dichloromethane (2×20 mL). The combined organics were dried (sodium sulphate) then evaporated to give a brown gum (210 mg) which was purified by column chromatography on neutral alumina (Grade 3) using dichloromethane/methanol (100:1). The title compound free base was obtained (90 mg, 35%) as a yellow oil. The hydrogen oxalate salt had mp 95°-97° C. (propan-2-ol/diethyl ether). $R_f=0.35$ in dichloromethane/methanol (20:1) on alumina plates; MS, m/z 215 for M+ of free base; $^1$H NMR (360 MHz, D$_2$O) δ 0.97-1.17 (4H, m, 2×cyclopropyl-CH$_2$); 1.52-1.64 (1H, m) and 1.84-1.92 (1H, m, 5-CH$_2$); 2.17-2.25(1H, m, cyclopropyl-CH); 3.25-3.55 (5H, m), 3.65-3.73 (1H, m) and 3.83-3.89 (1H, m, 2-CH$_2$, 4-CH, 6-CH$_2$ and 7-CH$_2$); 3.98-4.04 (1H, m, 3-CH); 8.27 (1H, s, pyrazine-H); 8.38 (1H, s, pyrazine-H). (Found: C, 57.41; H, 6.22; N, 13.10. $C_{13}H_{17}N_3.C_2H_2O_4$. 0.5 H$_2$O requires C, 57.31; H, 6.41; N, 13.37%).

EXAMPLE 2

3-(6-Bromopyrazin-2-yl)-1-azabicyclo[2.2.2]octane Sesquioxalate

Hydrogen bromide in acetic acid (5.0 mL of a 30% solution) was added to 3-(6-chloropyrazin-2-yl)-1-azabicyclo[2.2.2]octane (613 mg, 2.74 mmol; EPA 327155) and the solution was stirred at room temperature for 3.5 days. The mixture was poured into 0.5M potassium carbonate (75 mL) then further basified with solid potassium carbonate and extracted with dichloromethane (five times). The solvent was evaporated and the residue redissolved in hydrogen bromide/acetic acid (5.0 mL) and left stirring for 14 hours. The mixture was worked up as described above and crude product purified by column chromatography on silica using 10% methanol in dichloromethane containing 1% ammonia to afford the title compound free base (289 mg, 39%) as a colourless oil. The sesquioxalate salt had mp 173°-177° C. (dec) (methanol). MS, m/z 267 for M+ of free base. (Found: C, 41.70; H, 4.29; N, 10.40; Br, 20.32. $C_{11}H_{14}BrN_3.1.5C_2H_2O_4$ requires C, 41.70; H, 4.25; N, 10.42; Br, 19.82%).

EXAMPLE 3

Anti-6-(5-Methoxypyrazin-2-yl)-2-azabicyclo[2.2.2]octane Oxalate a) 2-Bromo-5-methoxypyrazine Methanolic hydrogen chloride (0.8 mL of a 10M methanolic solution) was added to a stirred solution of 2-amino-5-bromopyrazine (6.96 g, 0.04 mol) in anhydrous methanol (125 mL). To this cooled (−10° C.) solution was added isoamyl nitrite (16.1 mL, 0.12 mol) and the reaction mixture was stirred at −10° C. for 1.5 hours then at room temperature for 2 hours. The solvent was evaporated and the residue partitioned between aqueous saturated sodium carbonate (50 mL) and dichloromethane (4×50 mL). The combined organics were dried (sodium carbonate) and evaporated to give a brown oil which was purified by column chromatography on silica using 5% ethyl acetate in petroleum ether (60-80) to afford 2-bromo-5-methoxypyrazine as a pale yellow solid (6.45 g, 85%).

b)
6-(5-Methoxypyrazin-2-yl)-2-azabicyclo[2.2.2]oct-5-ene Hydrogen Oxalate

To a stirred, cooled (−70° C.) solution of 2-bromo-5-methoxypyrazine (4.74 g, 25 mmol) in anhydrous diethyl ether (350 mL) was added t-butyllithium (29.4 mL of a 1.7M pentane solution, 50 mmol) at −70° C. After 20 minutes a solution of 2-benzyloxycarbonyl-2-azabicyclo[2.2.2]octan-6-one (6.19 g, 23.9 mmol; prepared by analogy with the method of Low and Borne, Eur. J. Med. Chem., 1980, 15, 229-235) in anhydrous diethyl ether (50 mL) was added and the mixture stirred at −78° C. for 1.5 hours then allowed to warm to room temperature and stirred for a further 1 hour. Water (50 mL) was added and the organic layer was separated. The aqueous was re-extracted with diethyl ether (2×50 mL), the combined organics dried (magnesium sulphate) then evaporated to give a brown oil which was purified by chromatography on silica using 35% ethyl acetate/petroleum ether (60-80) to afford the alcohol as a yellow solid (3.85 g, 44%), mp 105°-108° C.; MS, m/z 369 for M+. This alcohol (3.85 g, 10.4 mmol), di-t-butyl-dicarbonate (2.50 g, 11.5 mmol) and 10% palladium on carbon (300 mg) were combined in methanol (100 mL) and hydrogenated (50 psi) for 24 hours. The mixture was filtered and the solvent evaporated, then the residue was purified by column chromatography on silica using 35% ethyl acetate/petroleum ether (60-80) to afford 2-t-butyloxycarbonyl-6-(5-methoxypyrazin-2-yl)-2-azabicyclo[2.2.2]octan-6-ol (3.14 g, 90%) as a yellow gum. MS, m/z 335 for M+.

A solution of this alcohol (3.14 g, 9.4 mmol) in anhydrous tetrahydrofuran (100 mL) was added to a stirred suspension of potassium hydride (1.34 g of a 35% oil dispersion, 11.7 mmol) under nitrogen. After 0.5 hour carbon disulphide (0.84 mL, 14.1 mmol) was added at 0° C. followed after 10 minutes by iodomethane (0.73 mL, 11.7 mmol). The cooling bath was removed and the brown suspension stirred for 20 minutes then water (20 mL) was added. The tetrahydrofuran was evaporated and the residue partitioned between water (20 mL) and dichloromethane (3×50 mL). The combined organics were dried (magnesium sulphate) then evaporated. The residue was dissolved in toluene (100 mL) and the solution heated at reflux for 1 hour then evaporated to give a brown oil which was purified by column chromatography on silica using 10% ethyl acetate in dichloromethane.

2-t-Butyloxycarbonyl-6-(5-methoxypyrazin-2-yl)-2-azabicyclo[2.2.2]oct-5-ene was obtained (1.48 g, 73%) as a yellow gum. MS, m/z 317 M+. This olefin (1.07 g, 3.4 mmol) was dissolved in dichloromethane (50 mL) at 0° C. and trifluoroacetic acid (5 mL, 65 mmol) was added. This solution was stirred overnight then evaporated. The title compound free base was obtained as an oil (0.68 g, 92%). The hydrogen oxalate salt had mp 149°-151° C. (methanol/diethyl ether). MS, m/z 217 M+ of free base. (Found: C, 54.41; H, 5.72; N, 13.34; $C_{12}H_{15}N_3O.C_2H_2O_4$ requires C, 54.72; H, 5.58; N, 13.67%).

c) Anti-6-(5-Methoxypyrazin-2-yl)-2-azabicyclo[2.2.2]octane Oxalate

The foregoing olefin free base (580 mg, 4.5 mmol) was dissolved in methanol (40 mL) of Raney Nickel was added. The resulting suspension was heated at reflux for 20 minutes then the mixture was cooled and filtered. The solvent was evaporated and the residue purified by column chromatography on silica using dichloromethane/methanol/ammonia (80:20:1) to afford the anti isomer free base as a yellow oil (330 mg, 56%). The oxalate salt had mp 254°–257° C. (methanol). MS, m/z 219 for M+ of free base; $^1$H NMR (360 MHz, D$_2$O) $\delta$ 1.70–1.77. (1H, m) and 1.81–1.84 (3H, m, 7-CH$_2$ and 8-CH$_2$); 2.20–2.23 (3H, m, 4-CH and 5-CH$_2$); 3.34–3.40 (2H, m, 3-CH$_2$); 3.61–3.66 (1H, m, 6-CH); 3.68–3.70 (1H, m, 1-CH); 3.99 (3H, s, OCH$_3$); 8.19 (1H, d, J=1.2 Hz), and 8.26 (1H, d, J=1.2 Hz, 2 x pyrazine-H). (Found: C, 58.83; H, 6.82; N, 15.82. C$_{12}$H$_{17}$N$_3$O.0.5 (C$_2$H$_2$O$_4$) requires C, 59.08; H, 6.86; N, 15.90%).

EXAMPLE 4

Anti-6-(6-Methylpyrazin-2-yl)-2-azabicyclo[2.2.2]octane Hydrogen Oxalate a) 6-(6-Methylpyrazin-2-yl)-2-benzyloxycarbonyl-2-azabicyclo[2.2.2]octane

The title compound (666 mg) was prepared from 2-benzyloxycarbonyl-2-azabicyclo[2.2.2]octan-6-one and 2-iodo-6-methylpyrazine as described in Example 3. The alcohol obtained was dehydrated using potassium hydride, iodomethane and carbon disulphide as described in Example 3.

b) Anti-6-(6-Methylpyrazin-2-yl)-2-azabicyclo[2.2.2]octane Hydrogen Oxalate

The foregoing olefin (637 mg, 1.9 mmol) was hydrogenated (50 psi) overnight using 10% palladium carbon (280 mg) in methanol (30 mL). In order to complete the hydrogenation 20% palladium hydroxide on carbon (125 mg) was added and the mixture further hydrogenated (50 psi) for 3.5 hours. The mixture was filtered and the solvent evaporated. The residue was purified by column chromatography on silica using dichloromethane/methanol/ammonia (80:20:1) to first afford the syn isomer as a gum (227 mg, 59%) followed by the required anti isomer as a gum (48 mg, 12%). The hydrogen oxalate salt had mp 175°–178° C. (dec.) (methanol/diethyl ether). (Found: C, 56.87; H, 6.59; N, 14.07%. C$_{12}$H$_{17}$N$_3$.C$_2$H$_2$O$_4$.0.125H$_2$O requires C, 56.89; H, 6.56; N, 14.22%).

BIOLOGICAL ACTIVITY

| Compound of | Concentration | Change in IOP[a] |
|---|---|---|
| Description A | 0.005% | −4 |
| Description B | 0.5% | −6 |
| Description C | 0.05% | −2 |
| Description D | 0.05% | −4.5 |
| Description E | 0.05% | −3 |
| Description F | 0.05% | −2 |
| Example 1 | 0.05% | −5 |
| Example 2 | 0.05% | −5 |
| Example 3 | 0.5% | −3.5 |
| Example 4 | 0.5% | −3 |

FOOTNOTE:
[a]Maximum mmHg change in intraocular pressure

FORMULATIONS

The compounds of the Descriptions and Examples may be formulated as follows:

| Eye Drops | |
|---|---|
| The pharmaceutically acceptable salt of the active compound | 0.5% |
| Benzalkonium chloride solution | 0.02% v/v |
| Disodium edetate | 0.05% |
| NaCl | 0.8% |
| Water for injections | to 100% |

The formulation is sterilised by autoclaving.

What is claimed is:

1. A method for the treatment of glaucoma and/or for reducing intraocular pressure, which comprises administering to a patient in need of such treatment an effective amount of a compound of structural formula (I):

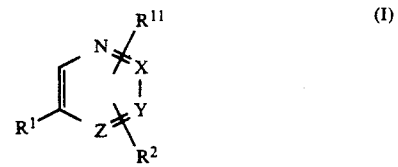

or a pharmaceutically acceptable salt or prodrug thereof; wherein one of X, Y and Z represents nitrogen and the remainder represent carbon atoms;

R$^1$ represents a non-aromatic azabicyclic ring system selected from:

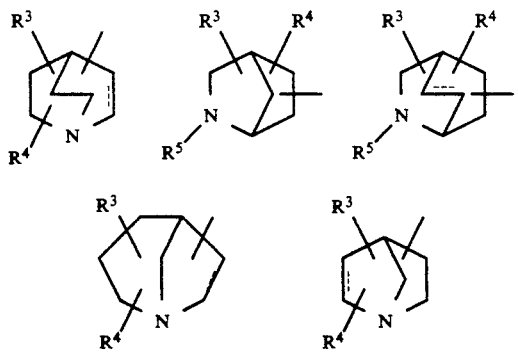

wherein the broken line represents an optional chemical bond;

the substituents R$^3$ and R$^4$ may be present at any position, including the point of attachment to the pyrazine, pyridazine or pyrimidine ring, and are independently selected from the group consisting of hydrogen, C$_{1-4}$ alkyl, halogen, C$_{1-4}$ alkoxy, hydroxy, carboxy and C$_{1-4}$ alkoxycarbonyl; or R$^3$ and R$^4$ together represent an oxo group; and R$^5$ represents hydrogen or C$_{1-4}$ alkyl; and $R^2$ and $R^{11}$ are independently selected from the group consisting of hydrogen, halogen, —$CF_3$, —$OR^6$, —$NR^6R^7$, —CN, $C_{1-8}$ alkyl and $C_{2-8}$ alkenyl; wherein $R^6$ is hydrogen or $C_{1-6}$ alkyl.

2. The method according to claim 1, wherein the compound administered is a compound of structural formula (IA):

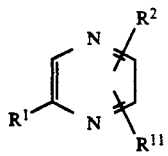
(IA)

wherein $R^1$, $R^2$ and $R^{11}$ are as defined in claim 1.

3. The method according to claim 1 wherein the compound administered is a compound of formula (II):

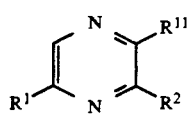
(II)

wherein $R^1$, $R^2$ and $R^{11}$ are as defined in claim 1.

4. The method according to claim 1 wherein the azabicyclic ring system $R^1$ is selected from the group consisting of azanorbornane, quinuclidine, isoquinuclidine, azabicyclo[2.2.2]octene and 1-azabicyclo[3.2.1]octane, any of which is optionally substituted with a group selected from methyl, hydroxy, fluoro, chloro and methoxycarbonyl.

5. The method according to claim 1 wherein $R^2$ and $R^{11}$ are independently selected from the group consisting of hydrogen, chloro, bromo, methyl, ethyl, isopropyl, cyclopropyl, methoxy, ethoxy, isopropoxy and n-butoxy.

6. A pharmaceutical composition adapted for topical administration to the eye which comprises an effective amount of a compound of formula (I) as defined in claim 1 or a pharmaceutically acceptable salt thereof or a prodrug thereof in association with a carrier suitable for topical administration.

7. The method according to claim 1, wherein the compound is selected from the group consisting of
exo-3-(6-methylpyrazin-2-yl)-1-azabicyclo[2.2.1]heptane; 3-(6-methylpyrazin-2-yl)-1-azabicyclo[2.2.2]octane;
exo-3-(3,5-dimethylpyrazin-3-yl)-1-azabicyclo[2.2.1]heptane;
endo-3-(5,6-dimethylpyrazin-2-yl)-1-azabicyclo[2.2.1]heptane;
3-(pyrazin-2-yl)-1-azabicyclo[2.2.2]octan-3-ol;
endo-3-(6-ethoxypyrazin-2-yl)-1-azabicyclo[2.2.1]heptane;
anti-6-(5-methoxypyrazin-2-yl)-2-azabicyclo[2.2.2]octane;
endo-3-(6-cyclopropylpyrazin-2-yl)-1-azabicyclo[2.2.1]heptane and
3-(6-bromopyrazin-2-yl)-1-azabicyclo[2.2.2]octane.

8. A pharmaceutical composition adapted for topical administration to the eye which comprises an effective amount of a compound of formula (I):

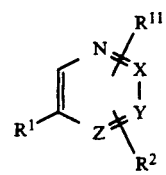

or a pharmaceutically acceptable salt or prodrug thereof in association with a carrier suitable for topical administration wherein
one of X, Y and Z represents nitrogen and the remainder represent carbon atoms;
$R^1$ represents a non-aromatic azabicyclic ring system selected from:

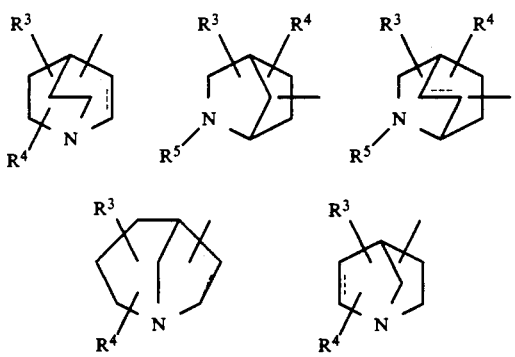

wherein the broken line represents an optional chemical bond;
the substituents $R^3$ and $R^4$ may be present at any position, including the point of attachment to the pyrazine, pyridazine or pyrimidine ring, and are independently selected from the group consisting of hydrogen, $C_{1-4}$ alkyl, halogen, $C_{1-4}$ alkoxy, hydroxy, carboxy and $C_{1-4}$ alkoxycarbonyl; or $R^3$ and $R^4$ together represent an oxo group; and $R^5$ represents hydrogen or $C_{1-4}$ alkyl; and
$R^2$ and $R^{11}$ are independently selected from the group consisting of hydrogen, halogen, —$CF_3$, —$OR^6$, —$NR^6R^7$, —CN, $C_{1-8}$ alkyl and $C_{2-8}$ alkenyl; wherein $R^6$ is hydrogen or $C_{1-6}$ alkyl.

* * * * *